(12) United States Patent
Samson-Villeger et al.

(10) Patent No.: US 8,349,315 B2
(45) Date of Patent: Jan. 8, 2013

(54) **USE OF *LACTOBACILLUS CASEI* FOR INCREASING THE PROTECTION PROVIDED BY THE INFLUENZA VACCINE**

(75) Inventors: Sandrine Samson-Villeger, Lyons (FR); Raphaëlle Bourdet-Sicard, Palaiseau (FR)

(73) Assignee: Compagnie Gervais Danone, Paris (FR)

( * ) Notice: Subject to any disclaimer, the term of this patent is extended or adjusted under 35 U.S.C. 154(b) by 534 days.

(21) Appl. No.: 12/527,214

(22) PCT Filed: Feb. 13, 2008

(86) PCT No.: PCT/FR2008/000181
§ 371 (c)(1),
(2), (4) Date: Feb. 1, 2010

(87) PCT Pub. No.: WO2008/129148
PCT Pub. Date: Oct. 30, 2008

(65) Prior Publication Data
US 2010/0129334 A1 May 27, 2010

(30) Foreign Application Priority Data
Feb. 16, 2007 (FR) ..................................... 07 01140

(51) Int. Cl.
*A01N 63/00* (2006.01)
(52) U.S. Cl. ................................................... 424/93.45
(58) Field of Classification Search ........................ None
See application file for complete search history.

(56) References Cited

U.S. PATENT DOCUMENTS
7,604,809 B2 * 10/2009 Postaire et al. ............ 424/206.1

FOREIGN PATENT DOCUMENTS
WO    WO 01/89541    11/2001
WO    WO 2006/124630    11/2006

OTHER PUBLICATIONS

Singleton et al., Arch. Intern. Med., 2005, vol. 165, No. 16, Abstract.*
de Vrese, et al., "Probiotic Bacteria Stimulate Virus-Specific Neutralizing Antibodies Following a Booster Polio Vaccination", European Journal of Nutrition, 44:7, 406-413, 2005.
Ogawa, et al. "Oral Immunoadjuvant Activity of *Lactobacillus casei* subsp. *casei* in Dextran-Fed Layer Chickens", The British Journal of Nutrition, 95:2, 430-434, 2006.
Yasui, et al., "Reduction of Influenza Virus Titer and Protection Against Influenza Virus Infection in Infant Mice Fed *Lactobacillus casei* Shirota", Clinical and Diagnostic Laboratory Immunology, 11:4, 675-679, 2004.

* cited by examiner

*Primary Examiner* — Kade Ariani
(74) *Attorney, Agent, or Firm* — Morgan, Lewis & Bockius LLP

(57) ABSTRACT

The invention relates to the use of *Lactobacillus casei* in orally administrable compositions for increasing protection against influenza after the influenza vaccine, by potentiating the humoral response generated by said vaccine.

16 Claims, 6 Drawing Sheets

Figure 1:
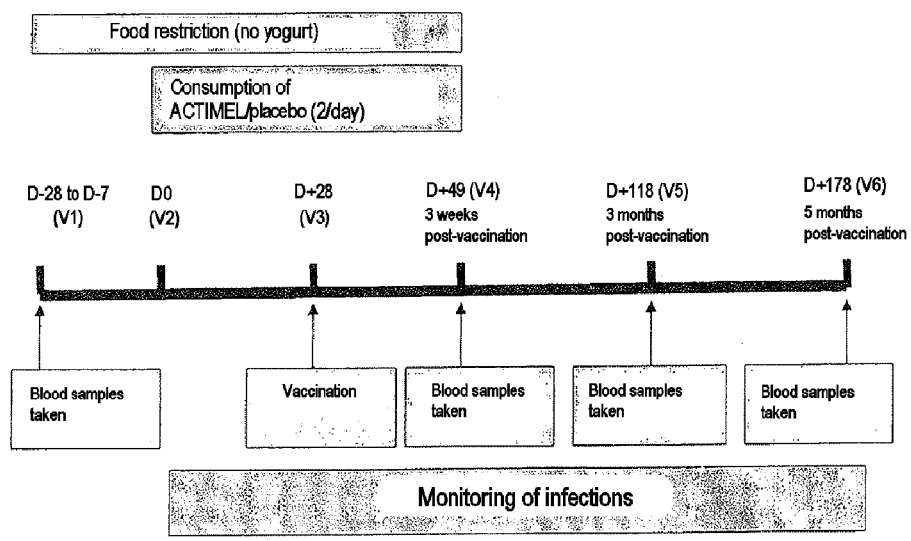

USE OF *LACTOBACILLUS CASEI* FOR INCREASING THE PROTECTION PROVIDED BY THE INFLUENZA VACCINE

RELATED APPLICATIONS

The present application is a U.S. National Phase Application of International Application PCT/FR2008/000181, filed Feb. 13, 2008, which claims the benefit of French Application No. 07/01140, filed Feb. 16, 2007, all of which are herein incorporated by reference in their entirety.

The invention relates to the use of *Lactobacillus casei* for potentiating the humoral response generated by influenza vaccination in elderly individuals and thus increasing protection against influenza after vaccination.

Influenza viruses (flu viruses) represent a major cause of respiratory infections.

Winter influenza epidemics affect 1 to 5% of the population, with very high infection rates in children and fatal complications in elderly individuals. Annual vaccination against influenza is recommended by the health authorities (in agreement with WHO) in individuals over the age of 65, individuals living in EHPAD (housing for the dependent elderly) or individuals with underlying health problems due to serious pathological conditions. Even in cases where vaccination does not prevent the disease, it makes it possible to reduce the severity, the duration and the risk of complication (superinfection, hospitalization, death) associated with influenza.

Nevertheless, although influenza vaccination confers, in the majority of adult individuals (70% to 90%), an antibody titer considered to be protective (anti-hemagglutinin titer greater than or equal to 40; WHO weekly epidemiological record, No. 33, p. 283, Aug. 19, 2005), the same is not true in the case of elderly individuals, where this antibody titer is reached only in 30 to 40% of individuals (COX et al., Scand. J. Immunol., 59, 1-15, 2004). This suboptimal response by elderly individuals to the influenza vaccine is due to functional defects in the immune system which are related to age and/or to the physiological condition of the individual (DENG et al., J. Immunol., 172, 3437-46, 2004; KANG et al., J. Immunol., 173, 673-81, 2004).

One way to improve the immune response is to administer immunostimulant substances which play the role of an adjuvant. Thus new vaccines containing adjuvants (such as MF59, which consists of stable droplets of size <250 nm, composed of squalene, metabolizable oil and two surfactants (polyoxyethylene sorbitan monooleate and sorbitan trioleate) in an oil-in-water emulsion) are beginning to be sold in France for potentiating the immune response of elderly individuals (BALDO et al., Vaccine, 19, 3472-5, 2001). Moreover, the diet can modulate immune responses. It has been shown that selenium and zinc supplements and certain vitamins and trace elements taken for 2 to 6 months can make it possible to increase the immune responses of elderly individuals in institutions in response to vaccination (ALLSUP et al., J. Am. Geriatr. Soc., 52, 20-4, 2004; BUNOUT et al., JPEN J. Parenter. Enteral. Nutr., 28, 348-54, 2004; BUNOUT et al., JPEN J. Parenter. Enteral. Nutr., 26, 372-6, 2002; CHANDRA, Lancet, 340, 1124-7, 1992; GIRODON et al., Arch. Intern. Med., 159, 748-54, 1999; LANGKAMP-HENKEN et al., J. Am. Geriatr. Soc., 52, 3-12, 2004; PROVINCIALI et al., Age Ageing, 27, 715-22, 1998). It has also been reported that certain probiotics can also modulate the response to vaccines, such as the poliomyelitis vaccine (DE VRESE et al., Eur. J. Nutr., 44, 406-13, 2005).

It has previously been observed (PCT application WO 2001/089541) that the administration of *Lactobacillus casei* can increase the cell-mediated immune response (mediated by T lymphocytes) with respect to various pathogenic microorganisms, among which is the influenza virus. On the other hand, the possible effects of *Lactobacillus casei* on humoral immunity, which is involved in the protection conferred by influenza vaccination, remain poorly understood.

The inventors have undertaken to study the effect of the ingestion of *Lactobacillus casei* on the change in specific serum antibody titers generated by influenza vaccination in elderly individuals. They have noted an increase in these antibody titers, resulting in particular in an increase in the frequency of seroconversion, and in the frequency of seroprotection.

"seroprotection" is defined as the presence, in an individual, of serum antibodies directed against an influenza virus, in an amount greater than or equal to a protection threshold. This protection threshold is defined as an anti-hemagglutinin serum antibody titer, measured by hemagglutination inhibition (HAI), of greater than or equal to 40. The "frequency of seroprotection", in a population, corresponds to the proportion of individuals in whom seroprotection is observed. It is generally accepted that a titer of antibodies measured by HAI and greater than or equal to 40 is related to protection against the strain involved and found in the vaccine (COX N. J. et al., Lancet, 1999: 354: 1277-82).

"Seroconversion" is defined herein as the increase, in an individual, in the amount of serum antibodies directed against an influenza virus, subsequent to vaccination against said virus, the post-vaccination antibody level being at least equal to 4 times the antibody level measured before vaccination. The "frequency of seroconversion" in a population corresponds to the proportion of individuals in whom seroconversion is observed.

The inventors have also noted that the positive effects of the ingestion of *Lactobacillus casei* on the change in serum antibody titers generated by influenza vaccination appear to be particularly marked in certain categories of elderly individuals, namely those displaying the lowest level of dependence, and those who are female.

The level of dependency was defined using the AGGIR (Autonomie Gerontologie Groupes Iso-Ressources [Gerontological autonomy, iso-resources groups]) classification grid (VETEL et al., Soins Gerontol., 23-7, 1998). Groups 1, 2 and 3 of the AGGIR grid group together individuals with high dependency; groups 4 and 5 group together individuals with low dependency; group 6 groups together individuals with no dependency.

Consequently, a subject of the present invention is the use of a bacterial strain of the *L. casei* species, for the preparation of an orally administrable composition for increasing protection against influenza after vaccination. The present invention also makes it possible to increase the humoral immunity conferred at the time of an influenza vaccination. It makes it possible to achieve in particular a protective antibody titer (seroprotection).

According to one preferred embodiment of the present invention, said composition is intended to be administered to elderly individuals aged 65 or over, receiving an influenza vaccination. Preferably, said individuals are at least 70 years old.

Particularly advantageously, said composition is intended to be administered to non-dependent individuals, or individuals with a low level of dependency and/or who are female.

In the context of the implementation of the present invention, said *L. casei* strain may be used alone, or in combination with other lactic acid bacteria of the *L. casei* species or of other species. Advantageously, it may be used in combination with yogurt ferments, namely *Lactobacillus bulgaricus* and *Streptococcus thermophilus*.

Preferably, a composition prepared in the context of a use in accordance with the invention contains at least $10^5$, preferably at least $10^6$, and generally between $1\times10^8$ and $1.5\times10^9$ *L. casei* cells per ml.

When *L. casei* is used in combination with yogurt ferments, said composition also advantageously comprises at least $10^7$, preferably between $2\times10^8$ and $1\times10^9$ *S. thermophilus* cells per ml, and at least $5\times10^5$ and preferably between $4\times10^6$ and $2\times10^7$ *L. bulgaricus* cells per ml.

An *L. casei* strain that is most particularly suitable for use in the present invention is the strain deposited on Dec. 30, 1994, with the CNCM (Collection Nationale de Cultures de Microorganismes [National Microorganism Culture Collection], 25 rue du Docteur Roux, Paris), under number I-1518.

Compositions prepared in accordance with the invention can be administered in the form of foods or food supplements. They may, for example, be milk products, and in particular fermented milk products comprising at least said *L. casei* strain, optionally combined, as indicated above, with other lactic acid bacteria, for example with yogurt ferments.

In order to obtain an optimal effect, said *L. casei* strain will preferably be administered for at least one week, preferably for at least 2 weeks, advantageously for at least 3 weeks, and entirely preferably for at least 4 weeks before the influenza vaccination. The administration of *L. casei* may subsequently be continued for as long as desired so as to maintain the increase in the immunity generated by the vaccination. The amount of *L. casei* administered daily will preferably be at least $10^{10}$, advantageously at least $2\times10^{10}$ CFU of *L. casei*. This amount can be administered in one or more daily intakes.

The present invention will be understood more clearly from the further description which will follow, which refers to a nonlimiting example illustrating the properties of a *Lactobacillus casei* strain for increasing the humoral immunity generated by an influenza vaccination.

EXAMPLES

A study was carried out in order to evaluate the effect of the consumption of a fermented milk product (Actimel®) containing *L. casei* CNCM I-1518, on the specific serum antibody titers generated by influenza vaccination, 3 weeks after vaccination (peak of the response between 2 and 4 weeks post-vaccination) and 3 and 5 months after vaccination (in order to monitor the change in serum antibody titers) with consumption of the product being stopped.

Summary of the Study

This study is a randomized, double-blind, placebo-controlled, multicenter pilot study. The 86 individuals were divided up into 2 balanced groups of 43 individuals, one group receiving Actimel®, the other group receiving the control product (placebo).

The course of this study is represented diagrammatically in FIG. 1.

The total duration of the study was 178 days.

The study comprised a selection visit (V1) aimed at selecting the elderly individual. This visit took place during the month preceding the inclusion visit (V2). The inclusion and the randomization of the individuals at V2 (D0) was carried out over 2 weeks for all the individuals of all the centers.

The consumption of the study product (Actimel® or control product according to the randomization) began for all the individuals at D0 (V2) and lasted 7 weeks (4 weeks before vaccination and 3 weeks after).

The individuals were all vaccinated against influenza (same batch of the Vaxigrip vaccine) by intramuscular injection in the deltoid muscle at D28 (V3), i.e. 4 weeks after the beginning of consumption of the study product.

Medical visits were carried out at D28 (V3), D49 (V4), D118 (V5) and D178 (V6).

Selection of Individuals

The individuals included in the study are elderly individuals residing in housing for the dependent elderly (EHPAD).

Inclusion Criteria man or woman at least 70 years old;

individual having an AGGIR score of between 2 and 5 (limits included);

individual having a titer of antibodies inhibiting the agglutination of guinea pig red blood cells by a strain related to the variant A/California/7/2004 (vaccine prototype) of less than 40 when the blood sample is taken at selection (V1);

individual having a body mass index (BMI) of between 16 and 27 kg/m$^2$ (limits included);

individual having given his or her written consent for his or her participation in the study and able to understand the information provided;

Noninclusion Criteria individual suffering from a serious and progressive pathology for which the life expectancy is less than 6 months;

individual with unbalanced type I or II diabetes;

individual with an allergy or hypersensitivity to milk proteins and/or to eggs;

individual with known lactose intolerance;

chronic or iatrogenic immunodepressed individual, in particular treated with oral corticosteroid therapy or immunosuppressors for more than 2 weeks over the course of the two months preceding selection (VI);

Randomization

The allocation of the individuals to the "Product" group or to the "Control" group was defined by a random draw, balanced between the two groups which were identified "A" or "B".

Two levels of stratification were determined according to the state of autonomy of the patients (thus reflecting the physiological condition of the individuals): the individuals having an AGGIR score (Autonomie Gérontologique Groupes Iso Ressources [Gerontological autonomy, iso-resources groups]) equal to 2 or 3 constitute the first stratum and the individuals having an AGGIR score of 4 or 5 constitute the second stratum.

Study Products

The Actimel® product is a commercial product.

The control product is a product having the same organoleptic qualities, the same acidity, the same energy value and the same texture as the Actimel® product, but which is free of lactic ferments. The 2 products were provided in anonymous bottles of 100 ml, and identified by means of a letter code (A or B).

The characteristics of these two products are summarized in Table I below.

TABLE I

| Product | Lipids g/100 g | Carbohydrates g/100 g | Proteins g/100 g | Energy KJ/100 g | Concentration of active ingredient (L. casei) |
|---|---|---|---|---|---|
| Actimel ® | 1.5 +/− 0.5 | 14.5 +/− 0.5 | 2.5 +/− 0.5 | 80-85 | >$10^8$ cfu/ml |
| Control | 1.5 +/− 0.5 | 14.5 +/− 0.5 | 2.5 +/− 0.5 | 80-85 | <1 cfu/ml |

Study Course

At the end of the selection visit, the individuals having all the inclusion criteria and none of the noninclusion criteria defined above were retained.

They were asked to abstain from consuming fermented milk products (yogurts, fromage blanc, petits suisses [unripened cream cheeses] and soybean yogurts) during the 7 days preceding the beginning of the study (between D-7 and D0) and until the visit V4 (D49).

A blood sample was taken in order to assay the basal anti-influenza antibody titer.

At D0, the inclusion and randomization visit (V2) was carried out.

Starting from D0, the individuals consumed, every day, the study product (A or B) assigned by the randomization at a rate of one bottle of 100 ml during breakfast, and one bottle of 100 ml during dinner, for 49 consecutive days.

At D28 (V3), the individuals were vaccinated against influenza by intramuscular injection in the deltoid muscle. The vaccine used (Vaxigrip) is an inactivated, split virion vaccine, each dose of which contains 15 μg of hemagglutinin of each of the following strains: 2 strains of type A (one H1N1 strain and one H3N2 strain), and 1 strain of type B; 15 μg of hemagglutinin per dose of each of these strains described. This vaccine does not contain adjuvant.

The H1N1 strain is the New Caledonia/20/99 strain; the H3N2 strain is the California/7/2004 strain, and the B strain is the Shangai/361/2002 strain (according to the WHO recommendations for vaccination in the Northern Hemisphere during the 2005-2006 season).

At each of the subsequent visits, carried out at D49 (V4), D118 (V5) and D178 (V6), a blood sample was taken in order to assay the serum antibodies specific for each of the strains present in the vaccine, generated by the influenza vaccination. A clinical examination was also performed, and the pathological conditions that had occurred or the treatments that had been taken since the previous visit were noted each time.

Assaying of Antibodies

Blood samples (1 tube of 7 ml) were taken from a vein in the forearm in all the individuals during visits V1, V4 and V5. The samples were taken on dry tubes, and then centrifuged so as to separate the serum. Each serum was aliquoted in cryotubes (500 μl per tube) so as to be stored at between −20° C. and −80° C. until the time the assays were carried out. These assays were carried out by the centre national de référence (CNR) [national reference center] for influenza viruses; Institut Pasteur, Paris, France.

The test used is the hemagglutination inhibition (HAI) test, carried out according to the WHO recommendations (WHO Manual on Animal Influenza Diagnosis and Surveillance: WHO/CDS/CSR/NCS/2002-5). This test is based on the ability of the anti-hemagglutinin antibodies specific for each viral strain which are contained in the serum tested, to bind to the hemagglutinin expressed at the surface of the viruses and to thus prevent the binding of these viruses to red blood cells. In the absence of specific antibodies, the formation of a network between the red blood cells and the virus is observed (culture well uniformly red). On the other hand, in the presence of specific antibodies, sedimentation of the red blood cells at the bottom of the well is observed.

Each serum was treated by incubation with RDE (receptor destroying enzyme) and then absorbed on rooster red cells in order to eliminate nonspecific agglutination due to the serum and not to the influenza virus. Each serum was serially diluted 2-fold, distributed into culture plates and incubated with a standardized viral suspension (4 hemagglutinin units per 50 μl). Guinea pig red blood cells were then added, so as to reveal the presence of viral hemagglutinin not neutralized by the antibodies.

Each test was validated by simultaneously assaying positive and negative controls originating from the CNR [national reference center] for the hemagglutination inhibition test.

The antibody titers are expressed as the inverse of the highest dilution still giving hemagglutination inhibition.

Statistical Analyses

The analysis of the data was carried out on the following populations and subpopulations:
  "Intention To Treat" (ITT) population comprising all the individuals included in the study, randomized and having received at least one of the products studied;
  subpopulations, according to the AGGIR stratum and according to gender.

The tests were carried out at the significance threshold of 5%, two-sided. A significance threshold of between 5% and 10% was considered to be indicative of a tendency.

The experimental plan is that of a parallel group with 2 "Product" versus "Control" groups.

Given the objectives of the study, the principal effect of this study is the "product".

The "AGGIR score", BMI, age and basal antibody titer effects were also studied.

For the antibody titer, it is known that this parameter is distributed according to a log-normal law. In order to carry out a parametric analysis, it is necessary to perform a log transformation on the antibody titers, and the normality of the antibody-titer logs was therefore verified and discussed.

The parametric analysis is a customary Gaussian model of analysis of variance and/or covariance according to the nature of the covariables.

The nonparametric analysis of variance and/or covariance (Friedman test) is carried out jointly.

The following covariables were taken into account in the analyses: "AGGIR score", BMI, age and basal antibody titer.

The comparison of the data between the products was carried out by means of a Chi-2 test or by means of a Fisher's exact test in the event of the conditions for use of the Chi-2 test not being adhered to. A logistic regression model was also implemented for taking into account the various effects ("AGGIR score", BMI, age and basal antibody titer).

This same analysis was also carried out for each stratification variable class ("AGGIR score").

Judgment Criteria

Principal Criterion for Effect of the Product Studied

The principal criterion selected is the influenza antibody titer at visit 4 (D49) with respect to the 3 viral strains.

The principal expression of this criterion is the variation in the antibody titer at visit 4 compared with the basal value.

Secondary Criteria for Effect of the Product Studied

The secondary criteria selected are, for each of the 3 viral strains:

the seroconversion (individual having an at least 4-fold increase in antibody titer compared with the basal level) at visit 4 (D49).

the seroprotection (individual having an antibody titer $\geq 40$) at visit 4 (D49).

Results

On the ITT Population

Antibody Titer

Figure 2:
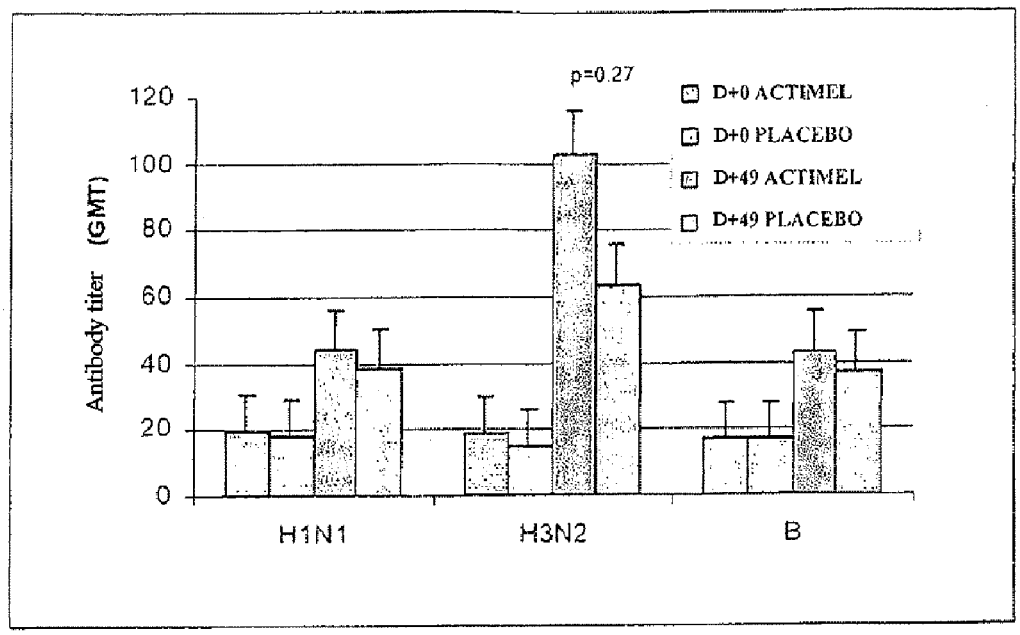

The results are illustrated by FIG. 2. These results show that the consumption of Actimel generates, 3 weeks after vaccination against each of the influenza strains, an antibody titer higher than that seen in the case of the consumption of the placebo.

Seroconversion

Figure 3:
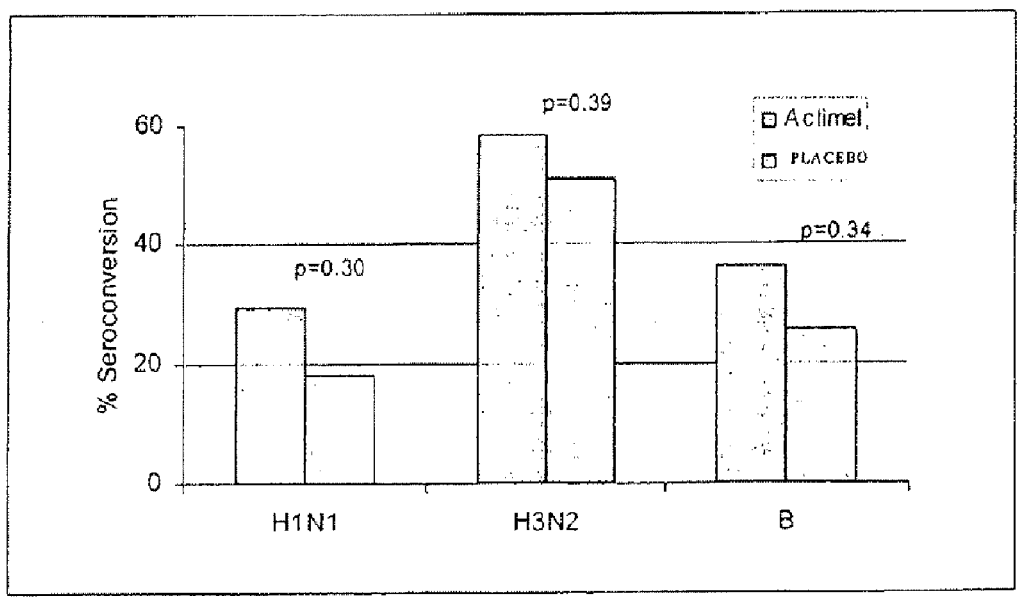

The results are illustrated by FIG. 3. These results show that the consumption of Actimel generates, 3 weeks after vaccination, a higher frequency of seroconversion, with respect to each of the influenza strains, than that observed in the case of the consumption of the placebo.

Seroprotection

Figure 4:
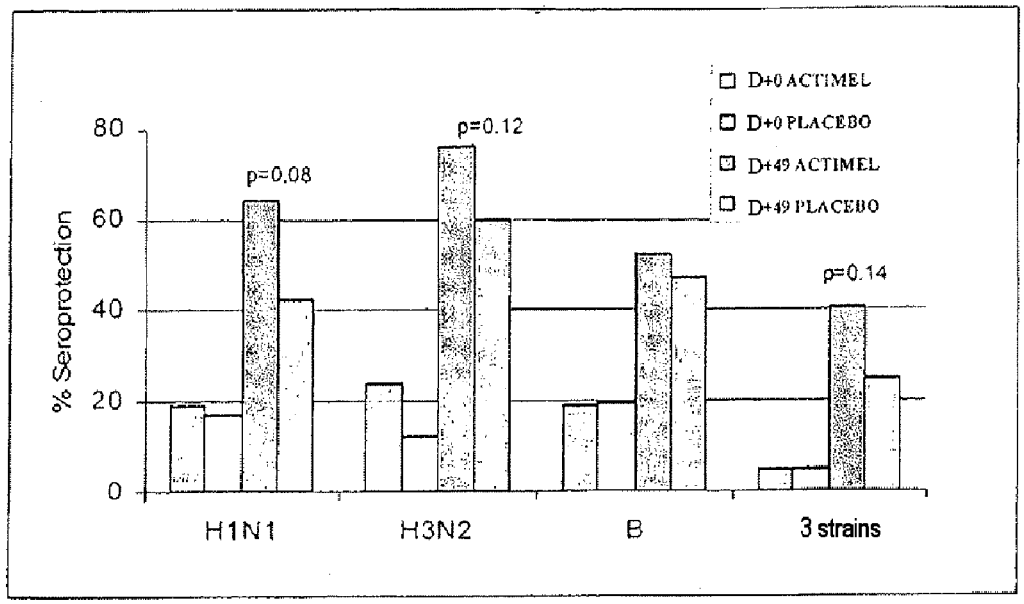

The results are illustrated by FIG. 4. These results show that the consumption of Actimel generates, 3 weeks after vaccination against each of the influenza strains, an increase in the percentage of protected individuals, compared with that observed in the case of the consumption of the placebo. This effect shows a statistical tendency in the case of the strain of H1N1 serotype.

On the Subpopulations

AGGIR 4-5 Subpopulation

Antibody Titer

Figure 5:
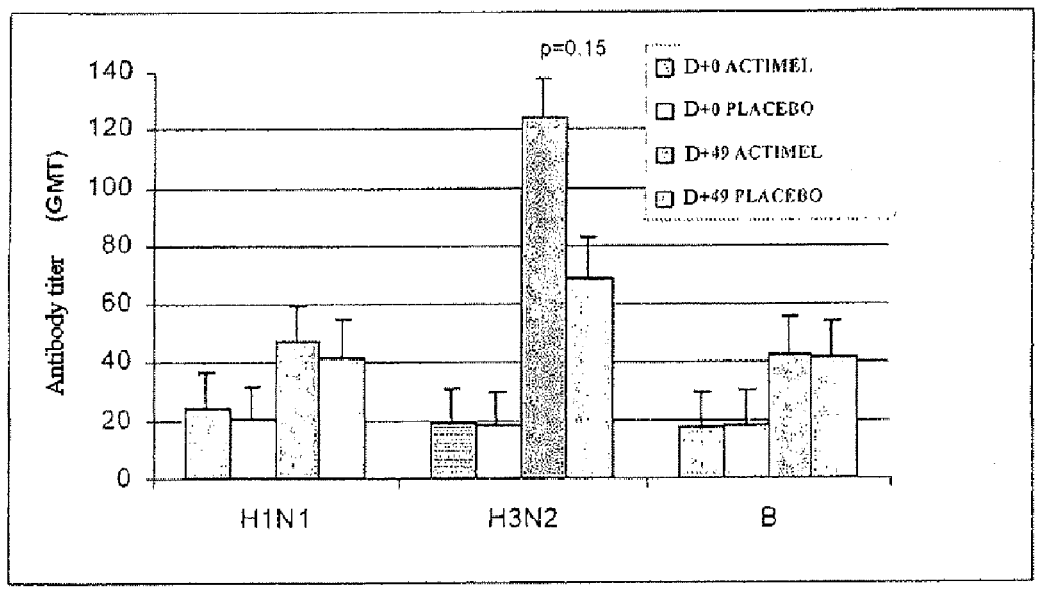

The results are illustrated by FIG. 5. These results show that the consumption of Actimel generates, 3 weeks after vaccination against each of the influenza strains, an antibody titer higher than that seen in the case of the consumption of the placebo.

Seroconversion

Figure 6:
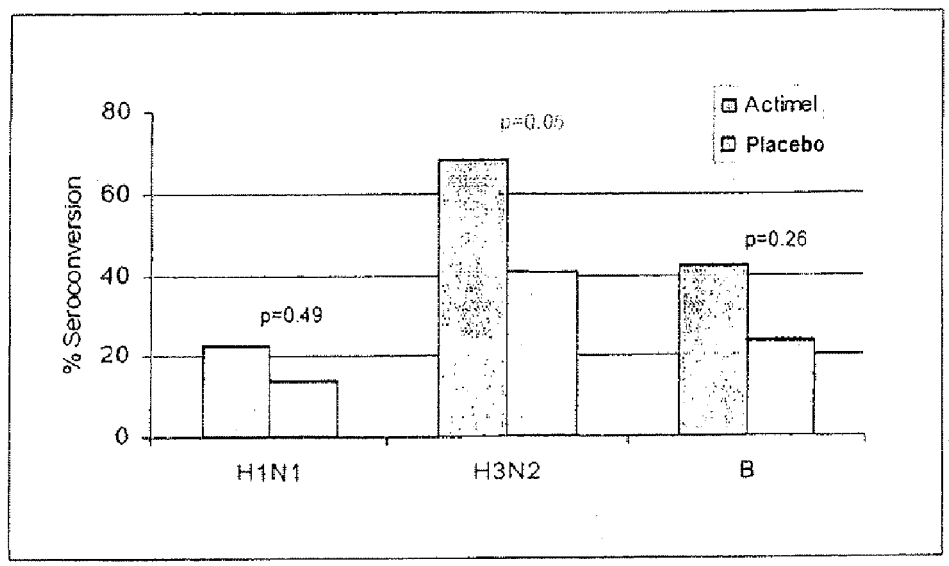

The results are illustrated by FIG. 6. These results show that the consumption of Actimel generates, 3 weeks after vaccination, a higher frequency of seroconversion, with respect to each of the influenza strains, than that observed in the case of the consumption of the placebo. This effect is statistically significant for the strain of H3N2 serotype.

Seroprotection

Figure 7:
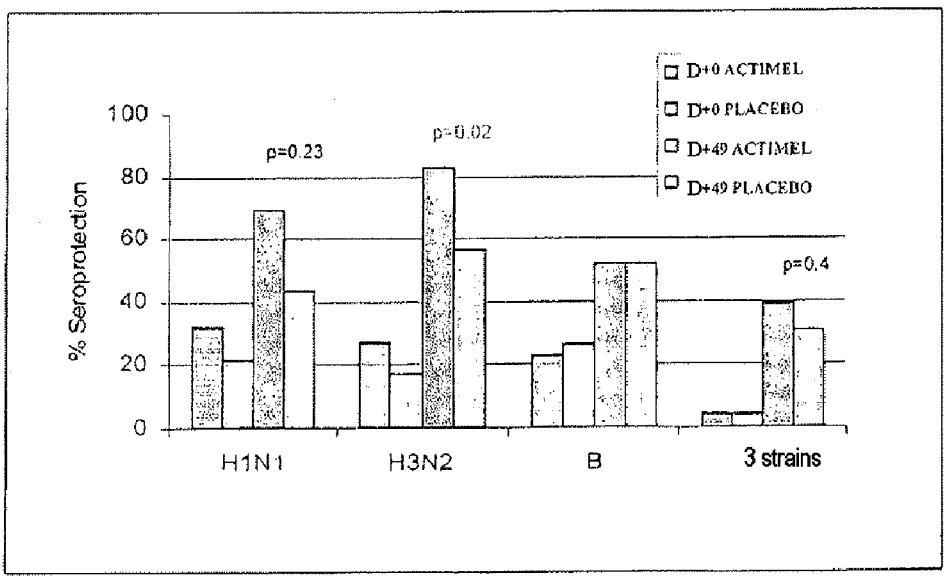

The results are illustrated by FIG. 7. These results show that the consumption of Actimel generates, 3 weeks after vaccination against each of the influenza strains, an increase in the percentage of protected individuals, compared with that observed in the case of the consumption of the placebo. This effect is statistically significant for the strain of H3N2 serotype.

Female Subpopulation

Antibody Titer

Figure 8:
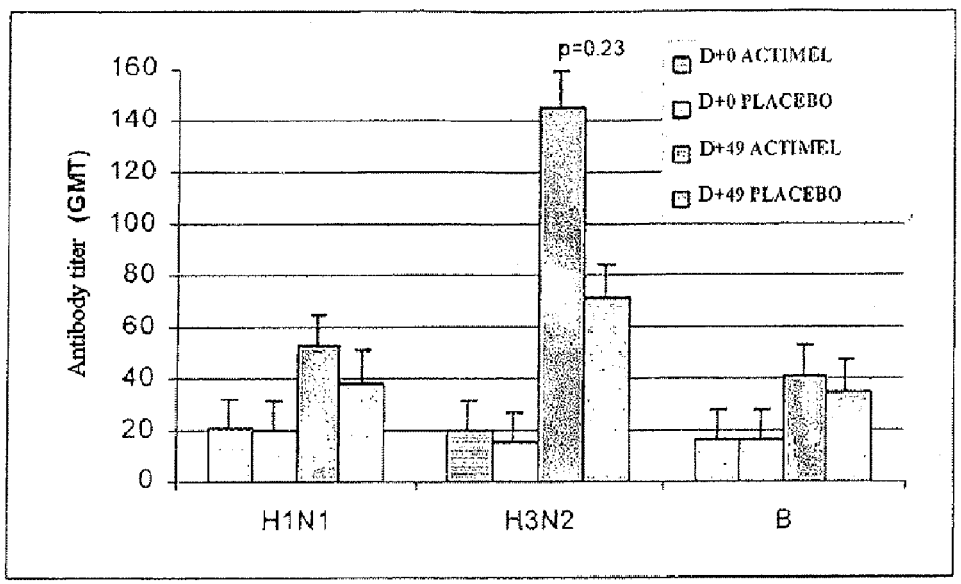

The results are illustrated by FIG. 8. These results show that the consumption of Actimel generates, 3 weeks after vaccination against each of the influenza strains, an antibody titer higher than that seen in the case of the consumption of the placebo.

Seroconversion

Figure 9:
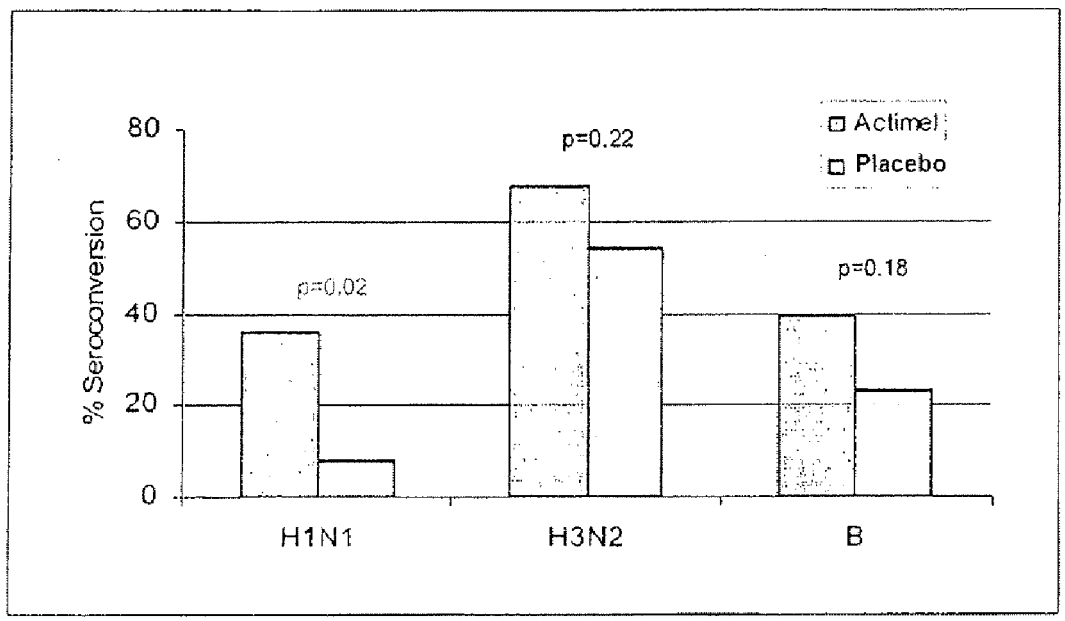

The results are illustrated by FIG. 9. These results show that the consumption of Actimel generates, 3 weeks after vaccination, a higher frequency of seroconversion, with respect to each of the influenza strains, than that observed in the case of the consumption of the placebo. This effect is statistically significant in the case of the strain of H1N1 serotype.

Seroprotection

Figure 10:
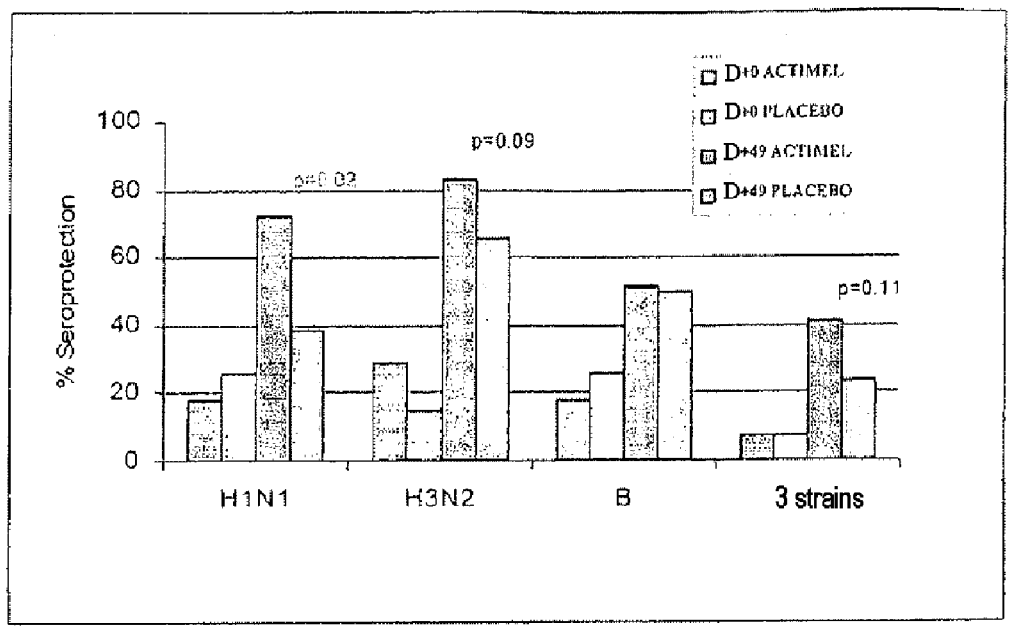

The results are illustrated by FIG. 10. These results show that the consumption of Actimel generates, 3 weeks after vaccination against each of the influenza strains, an increase in the percentage of protected individuals, compared with that observed in the case of the consumption of the placebo. This effect is more accentuated in the case of the strains of group A (statistical tendency for the H3N2 strain), and more particularly for the strain of H1N1 serotype (difference statistically significant).

The invention claimed is:

1. A method of increasing protection against influenza conferred at the time of an influenza vaccination comprising orally administering to an individual a composition comprising a bacterial strain of the *L. casei* species, wherein said composition is administered for at least one week prior to said influenza vaccination.

2. The method of claim 1, wherein the method increases the humoral immunity conferred at the time of vaccination.

3. The method of claim 1, wherein the individual is 65 years old or over 65 years old.

4. The method of claim 1, wherein said *L. casei* strain is CNCM I-1518 strain.

5. The method of claim 1, wherein the composition is in the form of a food or of a food supplement.

6. The method of claim 1, wherein the composition is in the form of a fermented milk product.

7. The method of claim 3, wherein said *L. casei* strain is CNCM I-1518 strain.

8. The method of claim 3, wherein the composition is in the form of a food or of a food supplement.

9. The method of claim 3, wherein the composition is in the form of a fermented milk product.

10. The method of claim 4, wherein the composition is in the form of a food or of a food supplement.

11. The method of claim 4, wherein the composition is in the form of a fermented milk product.

12. The method of claim 1, wherein said composition is administered for at least 4 weeks prior to said anti-influenza vaccination.

13. The method of claim 1, wherein said composition is administered daily in a quantity of at least $10^{10}$ C.F.U. (colony forming unit) of *L. casei*.

14. The method of claim 1, wherein said composition contains at least $10^5$ cells of *L. casei* per ml.

15. The method of claim 14, wherein said composition contains at least $10^6$ cells of *L. casei* per ml.

16. The method of claim 1, wherein said composition contains between $1 \times 10^8$ to $1.5 \times 10^9$ cells of *L. casei* per ml.

* * * * *